Figure 1:
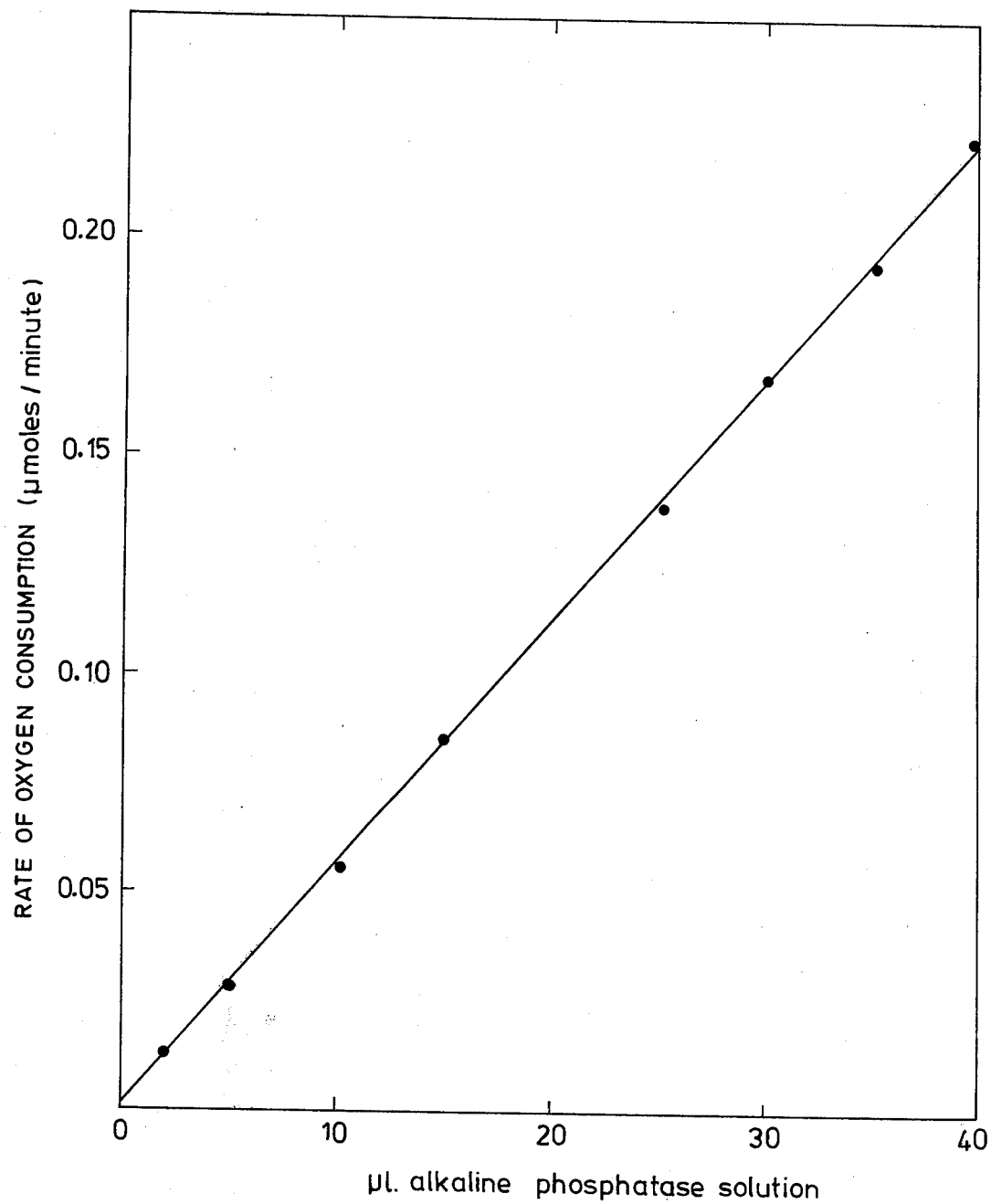

United States Patent [19]

Axcell et al.

[11] 4,059,490

[45] Nov. 22, 1977

[54] MEASUREMENT OF ALKALINE PHOSPHATASE LEVELS IN BODY FLUIDS

[75] Inventors: Barry Clifford Axcell, Johannesburg; Cyril Donninger, Sandton, both of South Africa

[73] Assignee: Chembro Holdings (Proprietary) Limited, Johannesburg, South Africa

[21] Appl. No.: 722,240

[22] Filed: Sept. 10, 1976

[30] Foreign Application Priority Data

Sept. 22, 1975 South Africa .................... 75/6003

[51] Int. Cl.$^2$ .................... G01N 31/14; G01N 33/00
[52] U.S. Cl. ................................ 195/99; 195/103.5 R; 195/127; 204/1 T
[58] Field of Search .................. 195/103.5 R, 99, 127; 204/1 E

[56] References Cited

U.S. PATENT DOCUMENTS

| | | | |
|---|---|---|---|
| 3,791,929 | 2/1974 | Hammer | 195/103.5 R |
| 3,933,593 | 1/1976 | Sternberg | 195/103.5 R |

OTHER PUBLICATIONS

Bergmeyer, "Methods of Enzymatic Analysis", 2nd Ed., vol. 2, Academic Press, Inc., N.Y. (1974), pp. 864–866.

*Primary Examiner*—Alvin E. Tanenholtz
*Assistant Examiner*—C. A. Fan
*Attorney, Agent, or Firm*—Beveridge, De Grandi, Kline & Lunsford

[57] ABSTRACT

A method of measuring the alkaline phosphatase level in a body fluid such as serum or plasma comprising hydrolyzing excess monophosphate ester dissolved in a suitable buffer by action of alkaline phosphatase in a predetermined volume of the body fluid to yield an oxidizable substrate, oxidizing the substrate with excess molecular oxygen in the presence of excess oxygenase and measuring the rate of oxygen consumption, preferably by means of an oxygen electrode. The invention also provides a reagent for use in this method which comprises a diethanolamine-HCl buffer having a molarity of 0.1 M to 4.0 M and a pH of 8.6 to 10.8 and containing magnesium ions in a concentration of 100 to 1000 $\mu$M and an excess of oxygenase.

15 Claims, 1 Drawing Figure

MEASUREMENT OF ALKALINE PHOSPHATASE LEVELS IN BODY FLUIDS

This invention relates to a method for the measurement of alkaline phosphatase levels in serum, plasma and other body fluids and to reagents used in the method. The measurement of alkaline phosphatase levels in body fluids especially in serum and plasma is well established as being useful and important in the diagnosis of certain pathological conditions such as rickets, osteomalacia, hyperparathyroidism, osteitis deformans and tumours of bone. Such measurements are frequently performed in the clinical pathology laboratory.

Prior art methods of determining alkaline phosphatase levels in body fluids include the following: Kay (J. Biol. Chem. 89, p 235, p 249, 1930) describes the use of gylcerophosphate as substrate for the measurement of plasma alkaline phosphatase. This method requires one ml of plasma incubated with glycerophosphate for 48 hours at 37° C. Free phosphate liberated by the hydrolysis is measured. A control using another 1 ml of plasma is necessary. Jenner and Kay (Brit. J. exp Path 13, 22 1932) improved the Kay method by shortening the incubation period to 3 hours by using glycine buffer at pH 8.8.

Bodansky (J. Biol. Chem. 101, 93 1933) describes a similar method in which barbitone buffer is used at pH 8.6 with a 1 hour incubation period.

King and Armstrong (Canad. med Ass. J. 31, 176, 1934) describe the use of phenylphosphate as substrate and measure the amount of liberated phenol. In a modification of this method, which uses a 30 min incubation period, Kine and Wootton (Micro-analysis in Medical Biochemistry 3rd Ed. London, J & A Churchill) introduced a phenylphosphate method requiring a 15 minute incubation period. Nitrophenyl phosphate has been used instead of phenyl phosphate (Ohmori, Enzymologia 4, 217, 1937, King and Delory, Biochem. J. 33, 1185, 1939, Bessey, Lowry and Brock, J. Biol. Chem. 164, 321 1946). The liberation of nitrophenol is measured by spectrophotometric methods.

Phenolphthalein phosphate has also been used in the measurement of alkaline phosphatase. On hydrolysis in alkaline medium a coloured product is produced which can be measured spectrophotometrically. (Huggins and Talalay, J. Biol. Chem. 159, 399).

According to the invention, a method of measuring the alkaline phosphate level in a body fluid comprises hydrolysing excess monophosphate ester dissolved in a suitable buffer by action of the alkaline phosphatase in a predetermined volume of the body fluid to yield an oxidisable substrate, oxidising the substrate with excess molecular oxygen in the presence of excess oxygenase, and measuring the rate of oxygen consumption.

The rate of oxygen consumption is proportional to the alkaline phosphatase level, i.e. activity, in the body fluid. From the rate of oxygen consumption, one can readily calculate the activity of the alkaline phosphatase present in the sample volume, and therefore the activity of the alkaline phosphatase in International Units ($\mu$moles/minute/liter) because a predetermined volume of body fluid is taken. The rate of oxygen consumption may be measured spectrophotometrically if the monophosphate ester is chosen to liberate a substrate which on oxidation by molecular oxygen produces a product with suitable absorption charcteristics.

Alternatively, it is preferred that the rate of oxygen consumption is measured by means of an oxygen electrode. The use of an oxygen electrode offers a number of distinct advantages. An oxygen electrode is relatively inexpensive and certainly very much less expensive than a spectrophotometer. It enables the oxygen consumption to be determined rapidly and in highly turbid or coloured solutions. The oxygen electrode is a polargraphic device for measuring the concentration of oxygen dissolved in a given medium and depends on the electrolysis of dissolved oxygen at a weakly negative electrode. The oxygen electrode has been known since the early part of this century. In 1956, Clark improved the electrode considerably by using an oxygen permeable, non-conducting membrane to isolate the electrolytic cell from the sample under measurement - Clark, L.C., Trans. Am. Soc. Art. Int. Org. 2, 41, 1956. Oxygen electrodes are commercially available. The oxygen electrode can be coupled in known manner to a standard recorder such as a Cimatic Cimapot T5 Recorder for following and recording the rate of oxygen consumption.

An excess of the monophosphate ester, molecular oxygen and oxygenase are used to ensure that the rate of oxygen consumption is proportional to the alkaline phosphatase level in the sample of body fluid being measured. It is possible to ensure that this excess of reagents is present because the range of likely alkaline phosphatase levels in body fluids is known.

Generally, the invention will be used to measure alkaline phosphatase levels in serum or plasma. The invention can, however, be used to measure alkaline phosphatase levels in other body fluids such as effusions. The body fluid may be obtained from the human or other animal by any known method.

The monophosphate ester will be one which is capable of being hydrolysed by action of the alkaline phosphatase to produce a substrate which can be oxidised by molecular oxygen in the presence of an oxygenase. The preferred monophosphate ester is catechol monophosphate which may have one or more other ring substituents provided, of course, the substituents do not render it unsuitable for the reaction.

Suitable buffers are those which do not inhibit either of the two reactions involved, i.e. hydrolysis and oxidation. The pH and molarity of the buffer for any particular system must be chosen to avoid any inhibition of these reactions. The buffer may contain sufficient magnesium ions or other suitable ions to serve as an activator for the alkaline phosphatase.

Suitable oxygenases for catalysing the oxidation are known in the art. Examples of suitable oxygenases in the case of catechol monophosphate ester are polyphenol oxidase, catechol 1,2-dioxygenase, catechol 2,3-dioxygenase, and catechol oxidase (dimerising).

In general, the oxygenase, the sample of body fluid, the buffer and the activator ions will first be placed in the reaction vessel and the reaction then initiated by addition of the monophosphate ester.

As is mentioned above, the preferred monophosphate ester is catechol monophosphate. With this ester the preferred buffer is a diethanolamine-HCl buffer having a molarity of 0.1 M to 4.0 M and a pH of 8.6 to 10.8. It has been found that this buffer provides for the optimum rate oxygen consumption thereby enabling the determination to be more rapidly. The preferred molarity is 2.0 M to 2.5 M and the preferred pH is 9.8 to 9.9. As an activator for the alkaline phosphatase, the reaction medium preferably contains magnesium ions in the range 100 to 1000 μM, particularly 500 μM.

As mentioned above, an excess of oxygenase must be present. Preferably, the oxygenase is present in such an amount that its activity is at least 500 times that of the alkaline phosphatase. The preferred oxygenase is polyphenol oxidase which may be stored in a tris(hydroxymethyl) aminomethane— HCl buffer of pH about 7.5. The molarity of this buffer will be very much less than, e.g. not exceeding 1% of, the molarity of the diethanolamine-HCl so that when the oxygenase is added to the reaction cell it does not have any significant effect on the pH of the diethanolamine-HCl buffer.

Thus, the invention provides, according to another aspect, a reagant for use in the above method which comprises a diethanolamine-HCl buffer having the pH and molarity as described above and containing magnesium ions in a concentration of 100 to 1000 μ molar, preferably 500 μ molar, and an excess of oxygenase, which is preferably polyphenol oxidase.

According to yet another aspect of the invention, there is provided a diagnostic kit for use in the above method which comprises
 a. a container containing diethanolamine-HCl buffer of pH 8.6 to 10.8 and molarity 0.1 M to ;b 4.0 M and containing 100 μM to 1000 μM magnesium ions;
 b. a container containing polyphenol oxidase in a tris(hydroxymethyl) aninomethane-HCl buffer of pH 7.5 and molarity not exceeding one percent of the molarity of the buffer of (a);
 c. container containing a salt of catechol monophosphate; and
 d. a container containing tris(hydroxymethyl)aminomethane-HCl buffer of pH 7.0 and molarity not exceeding one percent of the molarity of the buffer of (a).

The buffer of (a) preferably has the preferred pH and molarity as specified above.

The salt of the catechol monophosphate ester may be any known in the art, e.g. the diammonium or disodium salt.

An example of the invention will now be described. In this example, the following reagents were used:

1. Monophosphate ester — The monophosphate used was catechol monophosphate dissolved in 100 mM tris(-hydroxymethyl)aminomethane-HCl buffer, pH 7.0 containing 0.4% (v/v)chloroform. This yields catechol on hydrolysis by action of the alkaline phosphatase.

2. Oxygenase — The oxygenase used was polyphenol oxidase obtained from Worthington Biochemical Corp., Freehold, N.J., U.S.A. The specific activity of this oxygenase is 636 units per mg. (1 unit causes an increase in absorption (aΔA) at 280nm of 0.001/min. at 25° C and pH ;b 6.5 with tyrosine as substrate). The oxygenase was provided in a solution containing 200 units/100 μls in 5 mM tris(hydroxymethyl)aminomethane-HCl buffer of pH 7.5.

3. Alkaline phosphatase — The alkaline phosphatase was obtained from Miles-Seravac of Cape Town, South Africa. The phosphatase was prepared from calf intestine and had a specific activity of 2.2 units (1 unit is that amount of enzyme catalysing the liberation of 1 μmole phenol per minute at pH 8.8 and 25° C, using phenyl phosphate as substrate). The phosphatase was provided in a 100 diethanolamine-HCl buffer of pH 9.8 having an activity of 0.75 units/ml.

4. Buffer — The buffer used was a 2.0M diethanolamine-HCl buffer, ph 9.8.

The oxygen consumption of a number of samples of alkaline phosphatase of known concentration was measured using an oxygen electrode and the reagents mentioned above. The oxygen electrode was purchased from Clinical Sciences and Manufacturing Laboratories of Johannesburg. The oxygen electrode was connected to a circulating water bath maintained at 37° C. The electrode was covered by a 0.0005 inch Teflon (registered trademark) membrane and the cell volume was maintained at 1.5 ml. The output signal was recorded by a Cimatic Cimapot T5 Recorder.

The following reagents were added to the cell: 2 to 40 μls of the alkaline phosphatase solution, 100 μls of the polyphenol oxidase solution, 30 μls of 250 mM magnesium sulphate solution and sufficient of the diethanolamine-HCl buffer to bring the cell volume to 1.5 ml. Good results were obtained using 100 μls of the polyphenol oxidase solution which provided an activity of 200 units. It was found that the activity of polyphenol oxidase could vary from 100 to 500 units per 1.5 ml of cell volume for satisfactory results. The endogenous rate of oxygen consumption was measured in the absence of substrate and the reaction initiated by the addition of 50 μl of the solution of catechol monophosphate. The rate of oxygen consumption increased at a linear rate with time and the rate of reaction was measured for convenience over the initial part of the slope. By this means results were obtained within one minute of addition of substrate. Oxygen concentration in air saturated solutions was calculated by the method of Glasstone (Glasstone, S, Elements of Physical Chemistry, 1st Ed, pp 343 – 344, 1946 D. Van Nostrand Co. Inc., New York). The recorder was calibrated using air-saturated water.

Using this method, experiments were carried out using a range of 2 to 40 μls of alkaline phosphatase i.e. activities of 0.0015 to 0.030 units. The rate of oxygen consumption was recorded in each case and plotted, after deduction of a substrate blank, against concentration of alkaline phosphatase solution. The resulting graph is shown in FIG. 1. In this graph, the rate of oxygen consumption in μ moles/minute is plotted along the ordinate and the amount of alkaline phosphatase solution in μl is plotted along the abscissa. A linear regression analysis describes the relationship between the rate of oxygen consumption ($-dO_2/dt$) and alkaline phosphatase concentration by the equation:

$$\text{alkaline phosphatase} = 192.6 \, (-dO_2/dt) - 0.64$$

with a correlation coefficient of 0.990.

Using the above reagents and methods, it is possible to determine the alkaline phosphatase level in any given serum sample which will generally range from 50 to 100 μl. The sample of the serum of known volume is taken and using the above reagents and methods the rate of oxygen consumption is measured in μmoles/minute. From this rate it is possible to determine directly the activity of alkaline phosphatase in the sample volume by multiplying the oxygen consumption value by the appropriate factor to bring it to μmoles/minute/litre.

The method described above provides for rapid, accurate reproducible measurement of alkaline phosphate with plasma or serum volumes as low as 50 μl. As endogenous oxygen consumption is recorded before addition of substrate no sample is required for blank determination. Determinations can be made in highly turbid and coloured solutions and results can be obtained within one minute.

The method described above was compared with the method of Bessey & Lowry for the measurement of serum alkaline phosphatase. Results in international units were plotted against those obtained by the method of the invention on twenty four randomly selected samples of sera. The resulting plot had a correlation coefficient of 0.0967.

An example of a kit suitable for the measurement of alkaline phosphatase concentrations in the manner described above consists of the following:

a. A bottle of diammonium catechol monophosphate.

b. A bottle of 10 mM tris(hydroxymethyl)aminomethane-HCl buffer, pH 7.0.

c. A bottle of the oxygenase solution of (2) above.

d. A bottle of the buffer of (4) above.

We claim:

1. A method of measuring the alkaline phosphatase level in a body fluid comprising hydrolysing excess monophosphate ester dissolved in a suitable buffer by action of the alkaline phosphatase in a predetermined volume of the body fluid to yield an oxidisable substrate, said ester being a catechol monophosphate ester which may have one or more ring substituents, oxidizing the substrate with excess molecular oxygen in the presence of excess oxygenase and measuring the rate of oxygen comsumption.

2. A method according to claim 1 wherein the rate of oxygen consumption is measured using an oxygen electrode.

3. A method according to claim 1 wherein the oxygenase is polyphenol oxidase.

4. A method according to claim 1 wherein the buffer is a diethanolamine-HCl buffer having a molarity of 0.1 M to 4.0 M and a pH of 8.6 to 10.8.

5. A method according to claim 4 wherein the buffer has a molarity of 2.0 to 2.5 M and a pH of 9.8 to 9.9.

6. A method according to claim 4 wherein the buffer contains magnesium ions in a concentration of 100 to 1000 $\mu$M.

7. A method of measuring the alkaline phosphatase level in a body fluid comprising hydrolysing excess catechol monophosphate dissolved in a diethanolamine-HCl buffer having a molarity of 0.1 M to 4.0 M and a pH of 8.6 to 10.8 and containing magnesium ions in a concentration of 100 $\mu$M to 1000 $\mu$M by action of the alkaline phosphatase in a predetermined volume of the body fluid to yield catechol, oxidising the catechol and excess molecular oxygen in the presence of excess polyphenol oxidase and measuring the rate of oxygen consumption using an oxygen electrode.

8. A method according to claim 7 wherein the buffer has a molarity of 2.0 M to 2.5 M and a pH of 9.8 to 9.9.

9. A method according to claim 7 wherein the body fluid is selected from plasma and serum.

10. A method according to claim 8 wherein the body fluid is selected from plasma and serum.

11. A reagent for use in the method of claim 1 comprising a diethanolamine-HCl buffer having a molarity of 0.1 M to 4.0 M and a pH of 8.6 to 10.8 and containing magnesium ions in a concentration of 100 to 1000 $\mu$M and an excess of oxygenase.

12. A reagent according to claim 11 wherein the buffer has a molarity of 2.0 to 2.5 M and a pH of 9.8 to 9.9.

13. A reagent according to claim 11 wherein the oxygenase is polyphenol oxidase.

14. A diagnostic kit for use in the method of claim 1 comprising
   a. a container containing diethanolamine-HCl buffer of pH 8.6 to 10.8 and molarity 0.1 M to 4.0 M and containing 100 $\mu$M to 1000 $\mu$M magnesium ions;
   b. a container containing polyphenol oxidase in a tris(hydroxymethyl)aminomethane-HCl buffer of pH 7.5 and molarity not exceeding one percent of the molarity of the buffer of (a);
   c. a container containing a salt of catechol monophosphate; and
   d. a container containing tris(hydroxymethyl)aminomethane-HCl buffer of pH 7.0 and molarity not exceeding one percent of the molarity of the buffer of (a).

15. A kit according to claim 14 wherein the buffer of (a) has a molarity of 2.0 M to 2.5 M and a pH of 9.8 to 9.9.

* * * * *